United States Patent [19]

Tivolle et al.

[11] Patent Number: 4,584,746
[45] Date of Patent: Apr. 29, 1986

[54] DEVICE FOR DETECTING CRACKS IN STEEL SLABS LEAVING CONTINUOUS CASTING

[75] Inventors: Alain Tivolle, Martigues; Bernard Roumegoux, Entressen; Gérard Delhaye, Istres; Yves Codur, Marseille; Bernard Mittaine, Istres, all of France

[73] Assignee: Societe Lorraine et Meridionale de Laminage Continu - SOLMER, Puteaux, France

[21] Appl. No.: 566,194

[22] Filed: Dec. 28, 1983

[30] Foreign Application Priority Data

Jan. 28, 1983 [FR] France ................ 83 01511

[51] Int. Cl.$^4$ ............ B08B 3/02; G01R 33/12
[52] U.S. Cl. .................. 29/81 B; 29/81 A; 324/243
[58] Field of Search ........... 324/242, 243, 262, 238, 324/226; 29/81 B, 81 C, 81 A

[56] References Cited

U.S. PATENT DOCUMENTS

| 2,250,460 | 7/1941 | Barnes et al. | 324/262 X |
| 3,694,735 | 9/1972 | Mester | 324/226 X |
| 3,886,445 | 5/1975 | Chiba et al. | 324/243 X |
| 4,041,379 | 8/1977 | Karlsson | 324/242 X |
| 4,258,319 | 3/1981 | Shimada et al. | 324/242 X |
| 4,269,052 | 5/1981 | Imai et al. | 29/81 B X |
| 4,461,995 | 7/1984 | Harris | 324/226 X |

FOREIGN PATENT DOCUMENTS

| 0067935 | 4/1982 | European Pat. Off. . |
| 2027278 | 6/1970 | Fed. Rep. of Germany . |
| 2815228 | 10/1979 | Fed. Rep. of Germany ...... 324/262 |
| 2282640 | 3/1976 | France . |
| 2345252 | 10/1977 | France . |
| 2390729 | 12/1978 | France . |

Primary Examiner—Carl E. Hall
Attorney, Agent, or Firm—Balogh, Osann, Kramer, Dvorak, Genova & Traub

[57] ABSTRACT

A device for detecting cracks in steel slabs leaving continuous casting, which comprises two crack detecting units placed on either side of the passage of a slab leaving continuous casting and two descaling and cooling units located upstream of the detection units. Each detection unit comprises a mobile frame and a head which slides vertically with respect to the frame and which bears one vertical sensor and three horizontal sensors. The sensors are induction coils placed in a container which is surrounded by a forwardly open metal casing. One application of the device is the automatic switching of defective slabs towards a reprocessing unit.

13 Claims, 12 Drawing Figures

DEVICE FOR DETECTING CRACKS IN STEEL SLABS LEAVING CONTINUOUS CASTING

The present invention relates to a detector for detecting cracks in steel slabs leaving a continuous casting installation.

The technical sector of the invention is that of the iron and steel industry.

A continuous casting installation is used for casting numerous grades of steel, among which the medium carbon steels having a carbon content of between 0.08% and 0.2%, represent substantially twenty percent of the production.

Continuous casting of medium carbon steels presents difficulties due to the frequent appearance of surface defects or cracks which must absolutely be repaired before the slabs are drawn and rolled.

The solution consisting in systematically reprocessing all the slabs is very expensive, of the order of 30 to 50 Frs./tonne, and it is therefore of greatest interest to produce sensors which enable the cracks in the slabs to be detected on leaving continuous casting, in order to deflect towards subsequent reprocessing only those slabs which present cracks necessitating such treatment.

Crack detectors are known which are composed of induction coils supplied with alternating current and which are placed in the vicinity of a piece of steel. The alternating magnetic field develops in the steel eddy currents which react on the coil by a phenomenon of mutual induction. The presence of a crack substantially modifies the impedance and the eddy currents and brings about a variation in the amplitude of the excitation voltage of the coil and in the phase shift between the voltage and the excitation current of the coil.

Analysis of the excitation voltage of the coil by electronic circuits enables an electric signal to be furnished which presents a background noise in the absence of crack and which, in the presence of a crack, presents amplitude peaks such that the signal-to-noise ratio is greater than three and therefore enables a crack detection signal to be obtained.

Up to the present, crack detectors employing eddy currents have been used on relatively cold iron and steel products having a temperature less than 300° C. and a substantially flat surface which is not very rough.

Automatic switching of the slabs leaving continuous casting requires that the detection of the cracks be carried out on hot slabs, having a temperature of the order of 300° C. to 600° C., of which the surface is not very flat due to the deformations of the slab which circulates over rollers and of which the surface is very rough, comprising very sharp edges, for example caused by grains of steel which come from the preceding casting and which are welded to the surface of the slab.

It is an object of the present invention to provide a device for detecting cracks on the surface of a hot slab leaving continuous casting, with a view to controlling a device for automatically switching defective slabs towards a reprocessing unit intended to eliminate the cracks.

This object is attained by using induction coils generating eddy currents, of which the structure and mechanical assembly are designed so that, whatever the deformations of the slab and the roughness of the surface, the end of the coils is separated from the surface of the slab by a constant, very small distance, of the order of 4 to 5 mm, without this causing too rapid a wear of the sensors which must be able to withstand wear and tear and abrasion for the whole of a continuous casting campaign in order not to cause a stoppage of the continuous casting.

The air gap between the end of the core of a coil and the surface of the slab must be very small so that the coefficient of mutual induction is high, the signal-to-noise ratio is also high and the sensor is very reliable and detects all the defective slabs.

The coils of the sensors must be maintained and guided at a short distance from the surface of the slabs without interposing between the end of the coil and the surface of the slab any metallic piece which would disturb the magnetic circuits connecting the core of the coil to the slab. The width of the air gap must also remain constant whatever the shape and roughness of the surface to be monitored, as very slight variations in the width of the air gap would cause variations in the coefficient of mutual induction which would risk bringing about variations in the electric signal having amplitudes of the same order as the variations due to the cracks, hence a risk of deflecting, by error, slabs having no defects. The necessity of maintaining an air gap of constant width between the core of the coil and the surface of the slab leads to the necessity to mount the sensors on mobile supports which faithfully follow all the sinuosities of the surface and which temporarily retract in front of the rough parts with steep edge and such track of the surface must be ensured by applying the guide members of the sensors against the surface of the slabs with a very slight force, of the order of 1 Newton, in order to avoid creating a friction which would lead to very rapid wear of the guide members.

Another considerable difficulty to overcome is that of the temperature of the core and of the coil of the sensors which must remain substantially constant and low, of the order of 20° C., whilst the end of the coil is placed a few millimeters from the surface of a slab whose temperature may reach 600° C.

Temperatures higher than 20° C. would risk damaging the wires of the coil and the ferrite core and variations in temperature would bring about parasitic variations in the amplitude of the electric signal.

The objects of the invention are attained by means of a device which comprises two crack detection units which are disposed on either side of the passage of the slabs, and of which each bears one vertical sensor which is maintained above the upper face of the slab, in the vicinity of an edge, and a plurality of horizontal sensors which are located at different levels and which are maintained in the vicinity of a lateral face of the slab.

Each crack detection unit comprises a mobile frame which is equipped with vertical-axis casters and means for displacing the frame laterally with respect to the slab and to maintain the casters applied against a side of the slab.

This mobile frame comprises guide columns and each detection unit comprises a detection head which slides vertically along the columns and which bears the sensors and rollers of transverse horizontal axis which are maintained applied against the upper face of the slab by the weight of the sliding head and each detection unit further comprises a vertical single-acting jack which lifts the head at the end of a cycle.

Each sensor comprises an induction coil which is placed with clearance inside a mobile cylindrical casing having a ceramic bottom, of small thickness, which is interposed between the end of the coil and the slab and it comprises means for circulating cooling water in the clearance between the coil and the lateral wall as well as the bottom of the casing.

The mobile casing of each sensor comprises a hollow cylindrical body and a cap which is fixed to the front of the body, which cap is equipped with rollers whose axes are perpendicular to the longitudinal axis of the slab and which are mounted on supports which may slide parallel to the axis of the sensor.

The mobile casing of each sensor is guided axially by one or more ball bushes and it is pushed forwardly by a piston which moves with clearance in an axial bore and which is subjected to a forward thrust which is due to the loss of pressure produced by a leakage of air around the piston and which applies the rollers against the surface of the slab with a weak, constant thrust.

The invention results in the automatic detection of cracks in the steel slabs leaving continuous casting, particularly in medium carbon steel slabs, and the signal detecting a crack serves automatically to switch the defective slabs towards a unit for reprocessing them.

The devices according to the invention comprising a laterally mobile head make it possible to displace all the four sensors of each detection unit altogether to bring them closer to the slab at the beginning of a cycle or to move them away rapidly in the event of malfunctioning, in order to avoid deterioration of the device by the slab and at the end of the cycle.

Lateral displacement of the head also enables the detection device to be adapted to the different widths of the slabs.

The mobile casing which equips each sensor and which is pushed by a difference in pressure due to a leakage, makes it possible to displace each sensor individually and to apply it against the slab with a very weak thrust, so that each sensor follows the contour of the slab very faithfully, remaining at a constant distance from the surface thereof, without too considerable wear of the guide rollers.

The circulation of cooling water between the induction coil and the mobile casing which contains it enables the front end of the coil to be maintained at a distance of 4 to 5 mm from the slab, whilst maintaining the coil at a temperature of the order of 20° C.

The ceramic bottom of the mobile casing is of very small thickness, of the order of 1 mm, so that the presence of this bottom between the coil and the slab does not substantially reduce the coefficient of mutual induction between the slab and the induction coil and the sensitivity of the sensors to the cracks is very high.

The invention will be more readily understood on reading the following description with reference to the accompanying drawings, in which.

Figure 1:
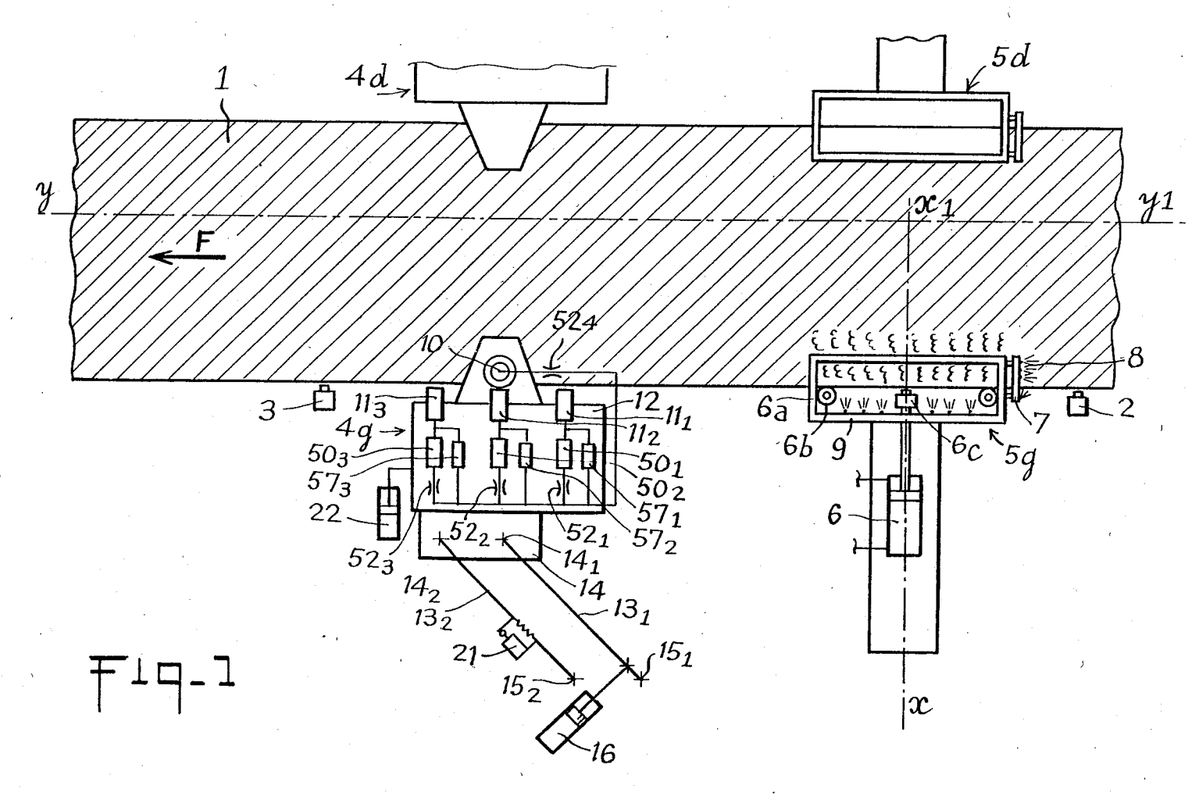
FIG. 1 is a schematic overall view of the detection device.

Referring now to the drawings, FIG. 1 represents a plan view of a steel slab 1 leaving a continuous casting installation. The direction of advance of the slab is shown by arrow F. The slab circulates over rollers. It is of substantially rectangular section. The upper face and the lateral faces of the slab are free.

The thickness of the slabs is constant, for example equal to 220 mm, the width may vary for example between 800 and 1500 mm and the device according to the invention must be adapted to the different widths of the slab. Moreover, the upper face and the lateral faces of the slab are not perfectly flat.

The slab presents undulations and it may be offset laterally, so that, for a slab of constant width, the upper face and the lateral faces present vertical or lateral displacements of which the amplitude may reach 10 cm.

One of the problems to be solved is to maintain sensors at a constant distance, of the order of 4 mm, from the faces of the advancing slab, despite the amplitude of the displacements of these faces, and this without mechanical or themal deterioration of the sensors.

A device according to the invention comprises, upstream, a first detector 2 detecting the presence of the slab which is for example a detector detecting the proximity of a metallic mass. At the end of casting, this detector emits an electric signal which indicates the end of advance of a slab and which automatically controls the retraction of the mobile detection units.

The device comprises, downstream, a second detector 3 of the same type as detector 2. At the beginning of a casting, detector 3 emits an electric signal which indicates the arrival of a slab and which automatically controls the beginning of a work cycle of the detection units.

The device comprises two mobile crack detecting units 4g and 4d disposed on either side of a slab.

The device comprises two descaling and cooling units 5g, 5d which are placed upstream of each respective crack detecting unit.

FIG. 1 shows only units 4g and 5g. Units 4d and 5d are identical to units 4g and 5g and they are symmetrical thereto with respect to the longitudinal axis y-y1 of the slab.

Each descaling and cooling unit may be displaced along a transverse axis x-x1 perpendicular to axis y-y1. Such displacement is controlled by a double-acting, rapid-return pneumatic jack 6 which comprises a hydraulic regulator for regulating the speed of approach of the slab. The jack 6 bears a mobile frame 6a supporting water injecting nozzles and pipes.

Upstream, the mobile frame bears descaling nozzles 7 which project jets of water 8 at very high pressure against the lateral face of the slab and against a band on the edge of the upper face. The water is compressed to about 150 bars. The nozzles are flattened and project flat jets which remove the oxidized cakes on the surface (scale).

The mobile frame further bears pipes 9 provided with flat jet nozzles which project jets of compressed water (at about 5 bars) against the lateral face and against a band on the upper face located along the edge in order to cool the surface of the slab to a temperature between 300° C. and 600° C.

The mobile frame bearing the pipes 7 and 9 is equipped with vertical-axis casters 6b which apply against the lateral face of the slab. It also bears a pneumatic sensor 6c which cuts off supply of the jack 6 when it detects the presence of the lateral face of the slab. The jack 6 then behaves as a pneumatic spring.

If, further to a lateral displacement of the slab, the sensor detects the absence of contact against the side of the slab, it opens pneumatic supply of jack 6 until the contact is re-established.

Each crack detection unit comprises four crack sensors, one vertical-axis sensor 10 which is located above the upper face of the slab, in the vicinity of the edge, and three horizontal sensors $11_1$, $11_2$ and $11_3$ which are located at three different levels spaced along the lateral face of the slab.

The assembly formed by the four sensors is mounted on a head 12 which may slide vertically with respect to a frame 14 which is supported by two arms $13_1$, $13_2$ forming a parallelogram articulated, on the one hand, on the frame 14 by articulations $14_1$ and $14_2$ and, on the other hand, on a fixed frame 15 by articulations $15_1$ and $15_2$. A jack 16 makes it possible to deform the articulated parallelogram to maintain the frame in abutment against the side of the slab. The jack 16 is a double-acting pneumatic jack with hydraulic speed regulator in the two directions of displacement.

Figure 2:
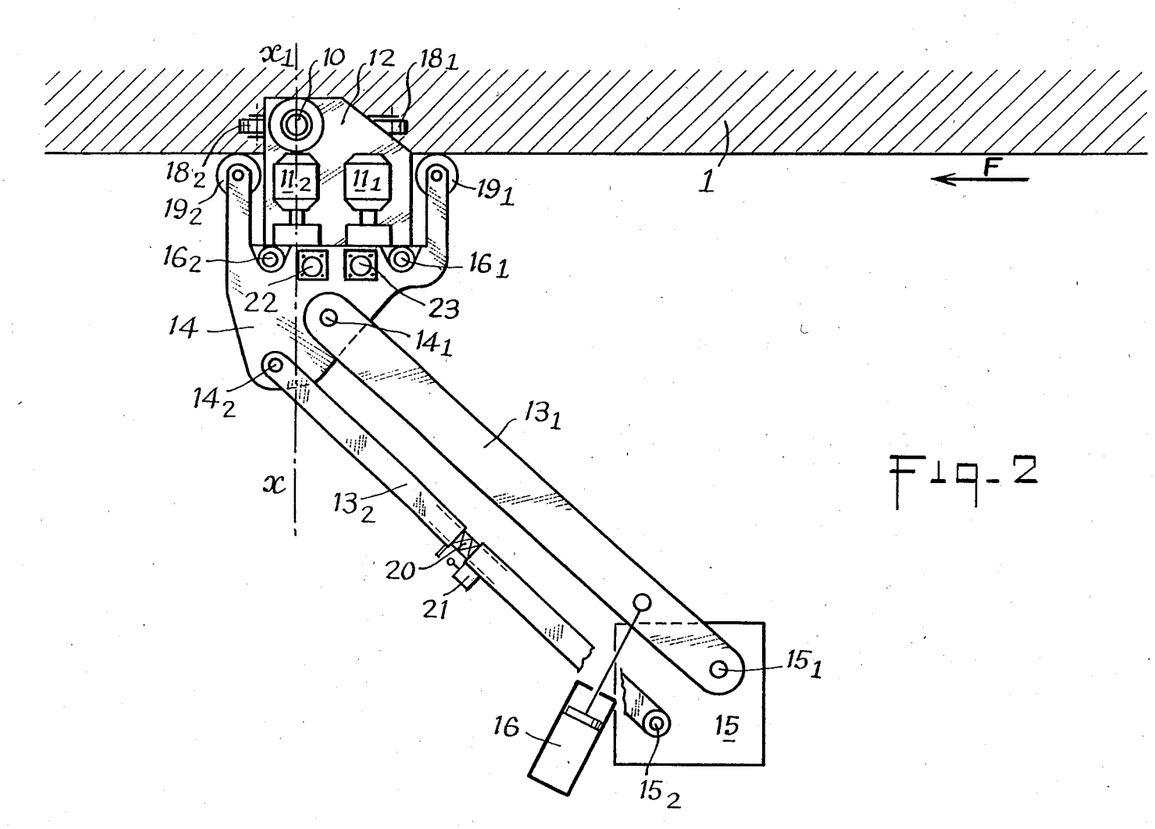
FIG. 2 is a plan view of a crack detection unit.

FIG. 2 is a plan view on a larger scale of a crack detection unit 4. This Figure shows the vertical sensor 10 and two of the lateral sensors $11_1$, $11_2$. The third sensor $11_3$ is located beneath sensor $11_1$. This Figure shows the head 12 bearing the four sensors. The head 12 is mounted to slide on two vertical guide rods or columns $16_1$, $16_2$ via ball bushes. These columns are borne by a frame 14 which is composed for example of two plates connected by vertical braces.

The mobile head 12 bears casters or rollers $18_1$, $18_2$ of horizontal axis perpendicular to the direction of displacement of the slab, which roll on the upper face of the slab 1 and which are maintained applied thereagainst by the weight of the mobile head.

The frame 14 comprises vertical-axis rollers or casters $19_1$, $19_2$ which roll against the lateral face of the slab and which are maintained applied thereagainst by the thrust of the jack 16 on the arm $13_1$.

Thanks to the articulated parallelogram, the frame 14 moves in translation parallel to the transverse axis x-x1. However, the horizontal sensors must be able to follow horizontal undulations of the lateral face and, to this end, the frame 14 must be able to pivot slightly by ±5°. This freedom of rotation is obtained thanks to a telescopic device which is mounted on the arm $13_2$ and which allows a slight variation in length of the latter.

The telescopic device 20 is equipped with a pneumatic displacement sensor which measures the variations in length of the arm $13_2$.

In the event of the rotation of frame 14 about axis $14_1$ exceeding a normal threshold which is of the order of ±5°, for example due to a defect in relief on the lateral face of the slab, the signal emitted by the sensor 21 automatically controls the retraction of the detection unit.

The frame 14 bears a vertical, single-action pneumatic jack 22 which lifts the mobile head 12 and which raises the latter in a position where the sensors are located above the slab. The jack 22 intervenes at the end of cycle or during cycle in the event of malfunctioning for example when the sensor 21 detects abnormal rotation.

At the beginning of cycle, pneumatic supply of the jack 22 is cut off and the head 12 then descends by gravity. A hydraulic regulator 23 is associated with the jack 22 to regulate the speed of descent of the mobile head.

The foregoing description explains the overall movements of the crack monitoring unit independently of the individual movements of the sensors which will be explained hereinafter.

At the beginning of a cycle, the parallelogram $13_1$, $13_2$ is retracted by jack 16 and the mobile head is lifted by jack 22, so that the sensors are placed above the slab and on the side thereof.

When sensor 3 detects the beginning of passage of a slab, it emits a signal which automatically controls the beginning of a cycle, the jack 6 is supplied and it brings the frame bearing the descaling and spray pipes nearer the slab.

Jack 16 is supplied and it pushes arm $13_1$ until the rollers $19_1$, $19_2$ come into abutment against the side of the slab. Jack 16 remains normally supplied for the whole cycle in order to maintain the rollers applied against the slab.

Supply of the jack 22 is then cut off and the mobile head 12 descends by gravity along the guide columns $16_1$, $16_2$ until the rollers $18_1$, $18_2$ roll against the upper face of the slab. The rollers $18_1$, $18_2$ are maintained in contact with the slab by the weight of the mobile head. The mobile head is then in work position.

From this position, individual members for displacing the sensors intervene, which constitute a second degree of positioning of the sensors making it possible to follow the faces of the slab with high precision, by employing very weak bearing forces and pressures, so that the sensors follow the contour of the slabs very faithfully, without any inertia.

Figure 3:
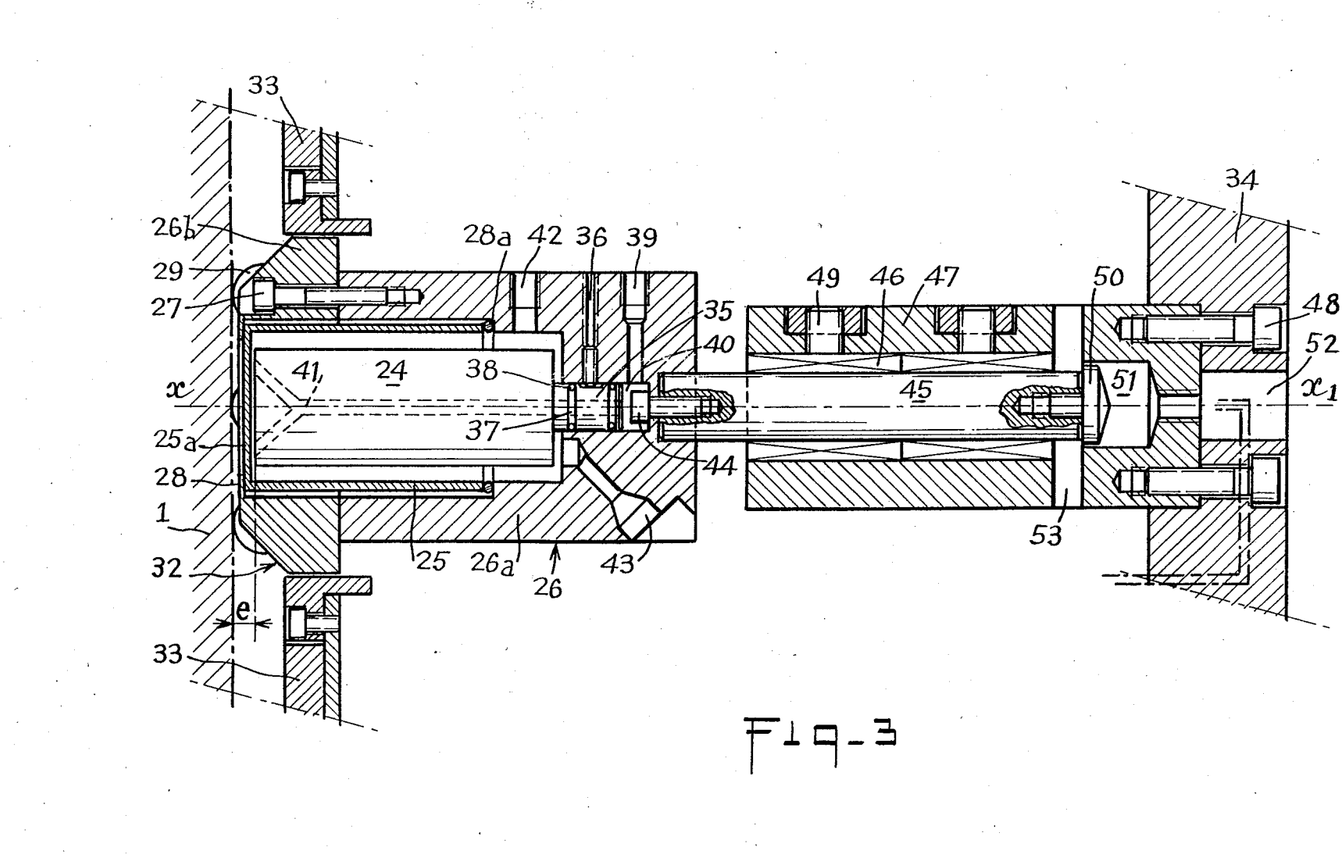
FIG. 3 is an axial section through a crack sensor.

FIG. 3 is an axial section through one of the crack sensors $11_1$, $11_2$ or $11_3$ and of the horizontal displacement device for maintaining the latter in contact with the side of the slab 1.

Each sensor comprises an induction coil 24 which is composed of a ferromagnetic core, for example a ferrite core surrounded by a coiled circuit.

The induction coil 24 is placed inside a container 25 made of refractory ceramics, for example very pure alumina with 99% alumina.

Container 25 is in the form of a cylindrical glove finger which surrounds the coil 24 and which is closed by a bottom 25a located at the front end or outer end, i.e. at the end placed in the vicinity of the slab. The bottom 25a is interposed between the front end of the coil and the side of the slab. The cylindrical lateral wall of the container 25 and the bottom 25a thereof are separated from the coil by a clearance which allows passage of cooling water.

The thickness of the walls and bottom of the container 25 is small, of the order of 2 mm for the walls and 1 mm for the bottom.

The assembly formed by the coil 24 and the container 25 is disposed inside a mechanical protection casing 26.

The casing 26 comprises a hollow cylindrical metal body 26a, for example a body of aluminium alloy and a cap 26b made of stainless steel which is fixed to the body 26a by screws 27 or by any other equivalent fixing means.

The cap 26b defines an inner bore which comprises, at the outer end, a very thin shoulder 28. This bore is extended by a bore coaxial to the cylindrical body 26a, having the same diameter, slightly larger than the outer diameter of the container 25 which is housed in this bore and which comes into abutment against the shoulder 28 and against a shoulder 28a of the casing.

Figure 4:
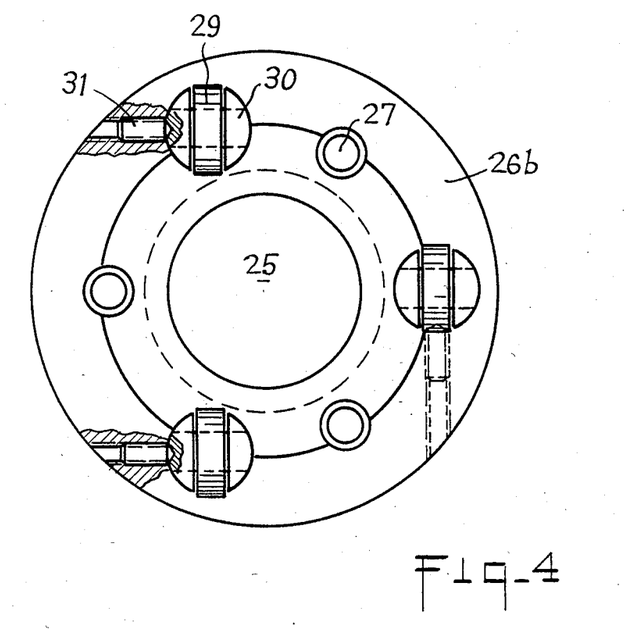
FIG. 4 is a front view of FIG. 3.

FIG. 4 is a front view of the cap 26b. It is seen that this cap is equipped with rollers or casters 29, three in number for example, disposed in a triangle, whose axes are perpendicular to the direction y-y1 of displacement of the slab. The pivot pin of each caster is mounted on a fork borne by a cylindrical support 30 which may slide in a bore pierced through the cap. A locking screw 31 makes it possible to block and unblock the supports 30 and to adjust the projection of the rollers with respect to the outer face of cap 26b.

At the start, the cylindrical supports 30 are fixed in a position such that the outer face of the cap lies at about 2 mm from the side of the slab. Sliding of the cylindrical supports 30 makes it possible to adjust the distance separating the outer face of the cap from the side of the slab to compensate wear of the rollers against the slab.

FIGS. 3 and 4 show that the cap 26b comprises a peripheral chamfer 32 which is cut to 45° and which projects beyond the rollers 29.

The slab may be rough, with pronounced relief and a leading edge substantially perpendicular to the surface of the slab, for example grains of cooled steel which remain on the continuous casting installation at the end of a casting and which adhere on the slab of a fresh casting. If one of these edges abutted against the edge of a sensor, the axial component of the thrust which it would exert on the casing of the sensor would be very low and would risk being insufficient to repel the sensor which would risk being seriously deteriorated. The chamfer 32 avoids this risk. It has an effect complementary of that of the displacement sensor 21 which controls the automatic retraction of the detection head assembly whilst the chamfers 32 repel each sensor individually.

In a variant, the rollers 29 may be replaced by guide shoes.

FIG. 3 shows a front plate 33 and a rear plate 34 which form part of the mobile head 12. Each sensor is mounted to slide parallel to its axis x-x1 with respect to the head thanks to a slide and bearing device which will be described hereinafter.

Beforehand, it will be indicated that the outer end of the core of each coil is extended by a cylindrical endpiece 35 which is engaged in an axial bore 40 in the body 26a and which is blocked therein by a screw 36 which makes it possible to adjust the axial position of the coil with respect to the casing 26 and with respect to the container 25. The endpiece 35 comprises peripheral grooves 37 in each of which is placed an O-ring 38 which ensures seal between the endpiece and the body of the casing. The body 26a comprises a cooling water admission channel 39 which opens out in the axial bore 40.

The endpiece 35 and the core of the coil comprise an axial channel 41 which conducts the cooling water up to the outer end of the core of the coil. The cooling water circulates in the free space between the coil and the container 25 and it is evacuated through an outlet channel 42 pierced through body 26a. Of course, the windings of the coil are protected from the water by being embedded in a resin.

The coil is supplied with A.C. voltage by conductors which pass through a duct 43.

The casing 26 of each sensor is fixed by a screw 44, or by any other equivalent fixing means, on a shaft 45 which is mounted in ball bushes 46.

The ball bushes 46 are mounted in a cylindrical body 47 which is fixed by screws 48 or by any other equivalent fixing means on the rear plate 34. The ball bushes are blocked in the body 47 by locking screws 49. These ball bushes resist rotation. They allow the axial displacements of the shaft 45 and prevent it from rotating. The shaft 45 bears at its outer end an axial jack or piston 50 which slides with clearance in a bore 51 which is connected by a duct 52 to a flow regulator (not shown in FIGS. 3 and 4 but shown schematically by references $52_1$, $52_2$, $52_3$ and $52_4$ in FIG. 1).

The duct 52 is supplied with compressed air under a pressure of the order of 3 bars.

The clearance between the piston 50 and the cylinder 51 is of the order of 0.1 mm.

Ducts 53 are pierced through the body 47 and the front end of the bore 51 thereby communicates with the outside.

The air arriving in bore 51 via duct 52 escapes through the clearance existing between the piston and the bore and leaves through ducts 53. The loss of pressure due to the leakage varies with the flow of air and it exerts an axial thrust on the piston 50 which is transmitted to the casing 26 and which maintains the rollers 29 applied against the slab. By adjusting the rate of flow by means of the regulators, the thrust is adjusted to a low value, of the order of 0.3 to 1.5 Newton. Thanks to this low value of the axial thrust, each sensor moves axially as soon as it is repelled axially even with a very weak force, so that it follows the contour of the slab very faithfully without the rollers 29 applying strongly thereagainst, which avoids rapid wear thereof.

Figure 5:
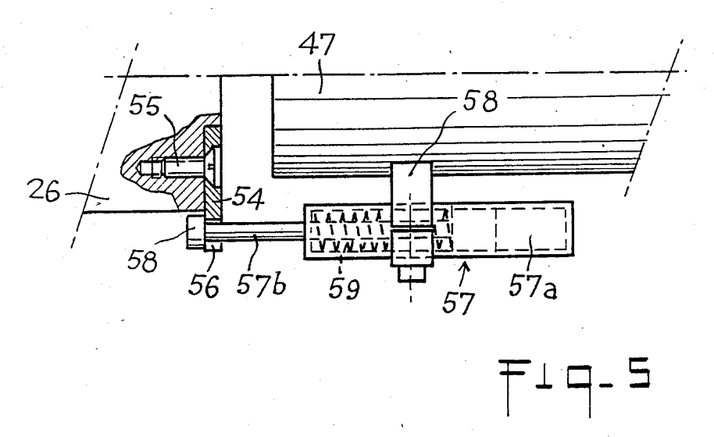
FIG. 5 is a partial axial section through a crack sensor with its return system.

FIG. 5 is a partial axial section of a sensor passing through a plane different from the plane of FIG. 3. This Figure shows the casing 26 and the cylindrical body 47. At the rear end of the casing 26, a plate 54 is fixed for example by screws 55. This plate projects beyond the cylindrical wall of the casing and the projecting end comprises a notch 56 or, in a variant, an oval hole.

Each sensor comprises a device for automatically retracting the sensor, which is constituted by a small single-acting pneumatic jack 57 whose cylinder 57a is fixed to the body 47 by a collar 58 or by any other equivalent fixing means. The rod 57b of the jack is parallel to axis x-x1 of the sensor. It passes through the notch 56. It bears at its front end a nut 58 forming a stop which abuts against the plate 54 when the jack is retracted. The cylinder of the jack contains a return spring 59 which tends to maintain the piston of the jack in rear position and which exerts on the piston an action antagonistic to that of the compressed air. The compressed air which supplies the jack 57 is the same as that which supplies the cylinder 51 of a sensor.

Operation is as follows:

At the beginning of a cycle, the compressed air is cut off and the piston of the jack 57 is maintained in retracted position by spring 59. The stop 58 therefore maintains the casing 26 of the sensor in retracted position in which the front face of the sensor is substantially in line with the front face of the front plate 33. The detection head positions itself and when it has taken its work position, the compressed air is sent onto the sensors, this having for its effect to compress the spring 59 and to repel the stop 58. The casing 26 is released and the rollers 29 are applied against the slab by the thrust on the piston 51 and they follow the contour of the slab.

In the event of accidental cut-off of the compressed air supplying both the auxiliary jack 57 and the axial jack 50, 51, the auxiliary jack is automatically returned rearwardly by spring 59 and the sensor is maintained in retracted position. The same occurs at the end of cycle.

Automatic retraction of the sensor might have been obtained by equipping the axial jack 50, 51 with a return spring, but in that case the spring would have exerted a force antagonistic to the thrust of the air during the whole cycle of operation, with the result that the force of abutment of the sensor against the slab would no longer have been constant.

The solution consisting in using an auxiliary jack 57 which displaces a stop 58 makes it possible to release the sensor entirely during a detection cycle, with the result that it is maintained applied against the slab by a very weak, constant force, which is easily adjustable and independent of any spring, therefore much more reliable.

FIG. 1 schematically shows the axial jack $50_1$, $50_2$, $50_3$, applying each horizontal sensor against the side of the slab and the auxiliary jack $57_1$, $57_2$, $57_3$ of each horizontal sensor. The flow regulators $52_1$, $52_2$, $52_3$, $52_4$ equipping the air admission of each axial jack are also shown.

Figure 6:
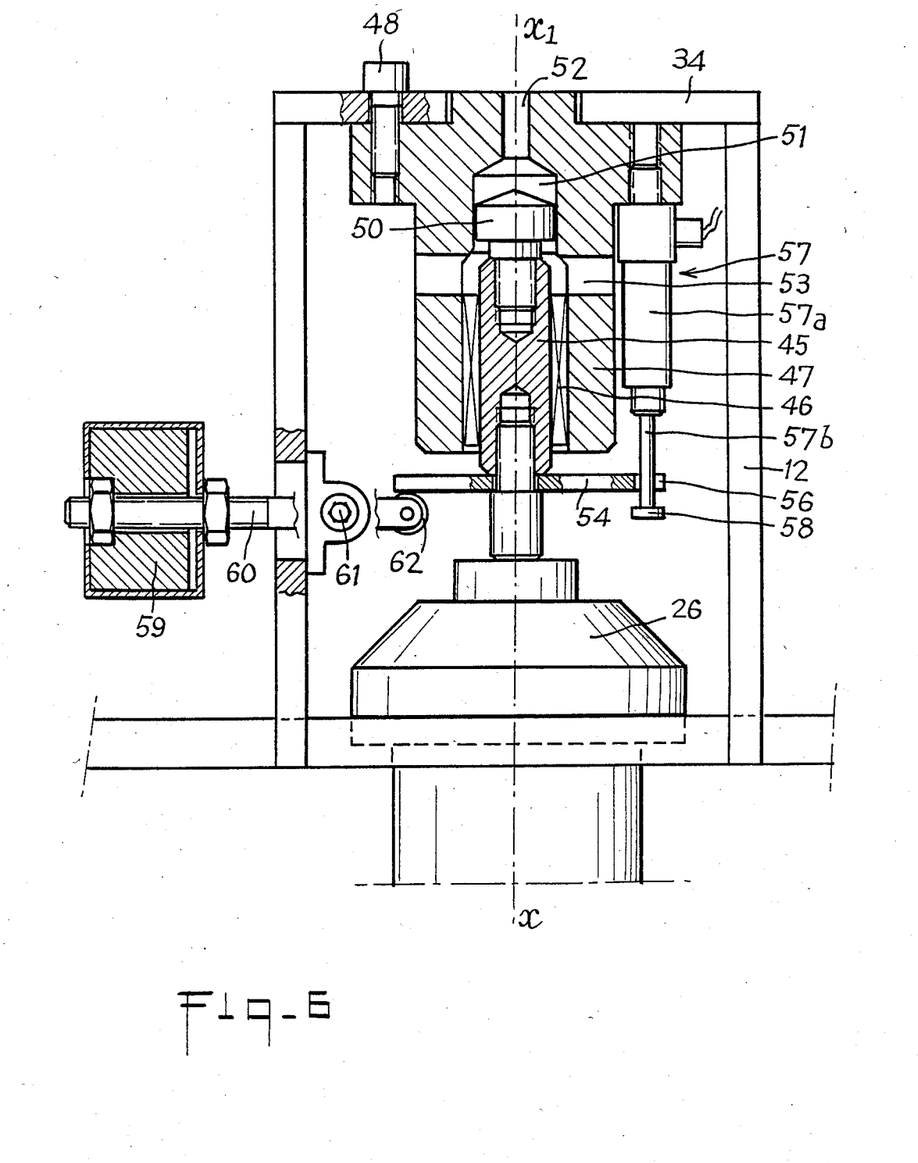
FIG. 6 is an axial section through the device for displacing a vertical sensor.

FIG. 6 is an axial section through the device for individually displacing the vertical sensor 10 equipping each detection head.

Those parts homologous to those of FIG. 3 are shown with the same references and they fulfill the same functions.

This Figure shows again the plate 54 which bears a notch 56 and bears a stop 58. Plate 54 is fixed directly to the pin 45 instead of being fixed to the casing 26, but its function is the same.

The only difference between the vertical sensor and the horizontal sensors lies in the presence, on a vertical sensor, of a counterweight 59 which is mounted on a lever 60 articulated about a horizontal pin 61. The lever arm which is opposite the arm bearing the counterweight bears a roller 62 which is maintained applied against the plate 54 by the action of the counterweight. The counterweight 59 is mounted on a threaded rod so that it may be displaced in order to adjust the torque exerted about the pin 61 in order to balance the weight of the sensor exactly. Thus, when the auxiliary jack 57 has released plate 54, the vertical sensor is maintained applied against the upper face of the slab solely by the constant thrust of the air against the piston 50 of the axial jack and the weight of the sensor, which is much greater than the thrust of the air, does not intervene in the bearing forces of the sensor which remain low, constant and adjustable.

The tubes supplying each sensor with cooling water and with compressed air are very supple tubes, for example small tubes made of silicone, which follow the displacements of the sensor by exerting thereon very weak elastic forces which are negligible with respect to the thrust exerted on the axial jack.

The area in which each sensor detects the presence of a crack is a substantially circular area having a diameter substantially equal to that of the coil. The sensor casings have an outer diameter of the order of 80 mm and the side of the slabs is 200 mm high.

The three horizontal sensors are placed at three different levels and they detect the presence of cracks over the whole height of the two sides of the slab. Of course, the number of horizontal sensors which scan the sides of the slab may be different from three.

On the other hand, the vertical sensors 10 detect the cracks only on two bands having a width of 80 mm located along the edges. The central part of the upper face and the lower face of the slabs are not scanned. A statistical study has shown that virtually on all the slabs comprising cracks, cracks are found in the vicinity of the edges of the slab and the adopted arrangement which is based on this statistical datum therefore enables all the slabs comprising important cracks to be reliably detected.

FIG. 3 shows that the end of each induction coil 24 is separated from the surface of the slab only by a film of cooling water and by the bottom 25a of the container 25 which has a thickness of the order of 1 mm.

The end of the coil is maintained at a constant distance e from the slab which is of the order of 4 to 5 mm. This short distance is necessary for the mutual induction between the coil and the slab to be high and the sensitivity to cracks to be high. Thanks to the cooling by water, the coil is maintained at a temperature of the order of 20° despite the proximity of the slab whose temperature is more than 300° C.

The ceramic container 25 whose bottom is interposed between the coil and the slab is a large element. The bottom 25a must be very thin and, despite this, the container must withstand mechanical and thermal stresses.

The ceramic of which the container is composed is very pure 99% alumina or weakly doped alumina, which has a good mechanical resistance to thermal shocks.

Each detection unit comprises a pneumatic detector detecting circulation of the cooling water of the induction coils.

A drop in water pressure automatically triggers off retraction of the detection unit. Similarly, each detection unit comprises a sensor sensing the temperature of the head. Beyond a temperature threshold, the sensor controls the retraction of the detection unit.

The installation comprises a sensor sensing the speed of the slab which delivers an electric signal proportional to the speed of advance of the slab. This electric signal is used for regulating automatic valves which control the rate of flow of cooling water, with the result that the rate of flow is proportional to the speed. When the speed of the slab is zero, the signal automatically controls retraction of the detection and cooling units.

FIGS. 7 to 12 show another embodiment of the device according to the invention.

Figures 7, 8:
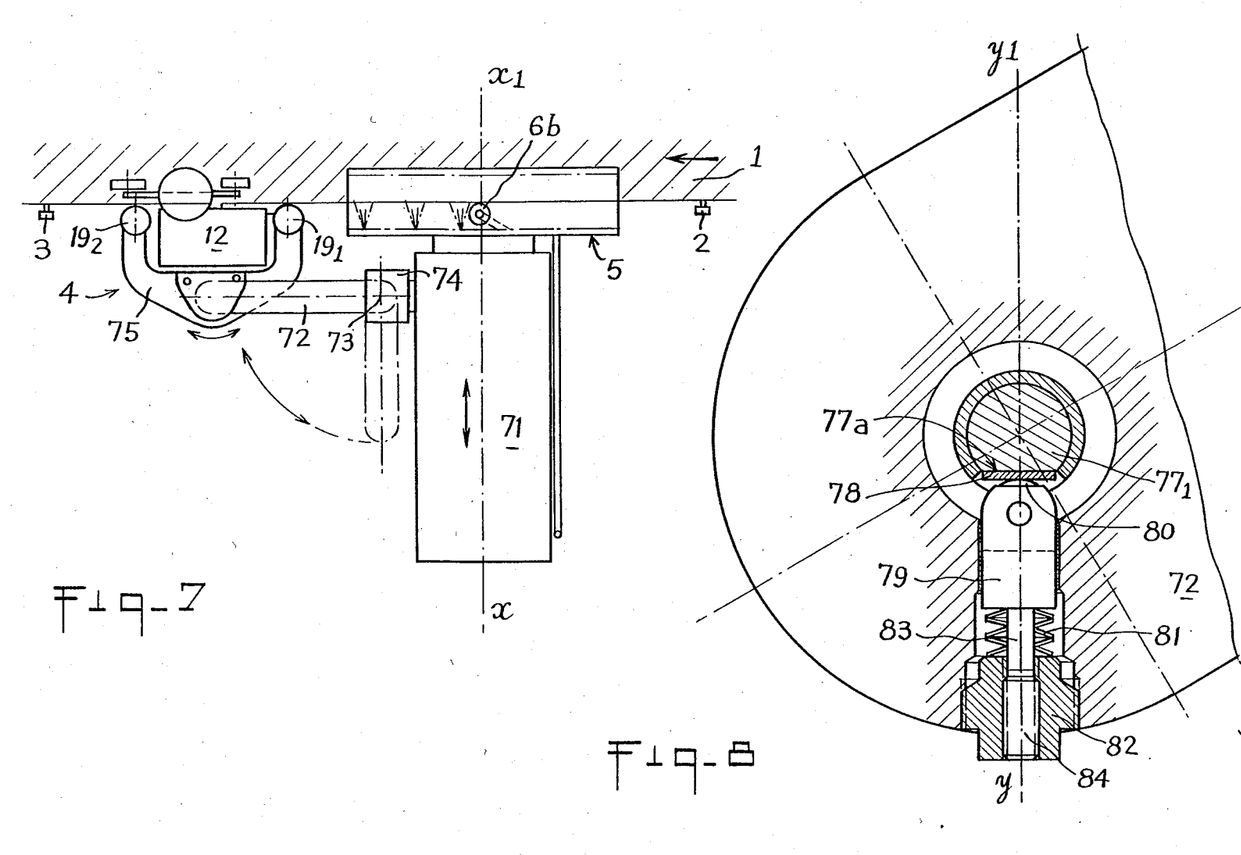
FIG. 7 is an overall plan view of a second device according to the invention.
FIG. 8 is a partial horizontal section through the end of the pivoting arm and the system for stopping rotation.

FIG. 7 shows a plan view. Homologous parts are shown with the same references.

The device comprises two identical units, symmetrical to the logitudinal axis of the slab and FIG. 7 shows one unit. This comprises a descaling and cooling unit 5 and a detection unit 4, which are both mounted on the same carriage 71 which is moved in translation along axis x-x1 perpendicular to the slab. The carriage 71 is displaced by a pneumatic double-acting jack associated with a hydraulic speed regulator.

The descaling and cooling unit 5 remains similar to the one which has been described. It comprises a vertical-axis roller 6b which is maintained applied against the side of the slab by the thrust of the jack which moves the carriage 71. When the roller 6b is in abutment against the slab, the supply pressure of the jack is reduced.

The detection unit 4, which will be described in detail, is mounted on a horizontal arm 72 which is connected to the carriage 71 by an articulation 73 of vertical axis. An oscillating pneumatic jack 74 drives the pivoting arm 72 and enables it to pivot through about 95° about the pin 73. The work position of the arm has been shown in solid lines and the rest position in chain-dotted lines.

Assembly of the detection unit 4 on a pivoting arm 72 which is articulated on the carriage 71 which also bears the descaling and cooling unit, presents the advantage that the longitudinal shift between the sensors and the cooling unit is constant, whatever the width of the slabs. The temperature of the slab beneath the sensors therefore remains substantially uniform and the precision of the electronic measurements is improved.

Assembly of the detection unit on a pivoting arm 72 enables the unit to be moved away from the slab by its pivoting through a quarter turn, this moving the unit away from the zone subjected to the radiation of the slab and facilitating maintenance operations on the detection unit.

The detection unit comprises a frame 14 which comprises a lower plate 75 in the form of a horse shoe bearing two vertical-axis casters or rollers $19_1$, $19_2$ which are maintained applied against the side of the slab by the torque exerted by the rotary jack 74.

The frame 14 comprises a lower plate 75 and an upper plate 76 which are connected together by three vertical columns 77.

FIG. 8 shows at $77_1$ one of the three columns which is fast with the lower plate 75 and with the upper plate 76 and which is connected to the free end of the shaft 72 by a device which allows freedom of rotation of the frame 14 with respect to the shaft of the order of ±7.5° with respect to the position of equilibrium. The shaft $77_1$ comprises a flat portion 77a on which is fixed a wearing part 78. The pivoting arm 72 bears a locking finger 79 of axis y-y1 which is disposed in a radial bore of the arm and which is equipped, at its front end, with a roller 80. The finger 79 is pushed forwards by an elastic member 81 formed for example by a stack of elastic washers or by a spring. A threaded stopper 82 makes it possible to adjust the pre-stress of the elastic member for example the compression of the washers.

The stopper 82 is pierced with an axial threaded bore in which penetrates a rod 83 fast with the finger 79. A screw 84 is screwed in the threaded bore and serves as adjustable stop for the rod 83.

Operation is as follows:

When the side of the slab is rough, it exerts thrusts on the rollers $19_1$, $19_2$ which create a torque which drives the frame 14 in rotation about shaft $77_1$. The finger 79 is repelled. It compresses the washers 81 until the rod 83 arrives in abutment, this limiting the angular amplitude to about 7.5°, on either side of the position of equilibrium in which the flat portion 77a is perpendicular to axis y-y1. The thrust of springs 81 on the finger 79 exerts on the shaft $77_1$ an antagonistic torque which tends to return the frame 14 to its position of equilibrium, as soon as the side of the slab becomes flat again and perpendicular to axis x-x1.

The device shown in FIG. 8 fulfills the same function as the telescopic device 20 of FIG. 2. Like the latter, the device according to FIG. 8 is equipped with an end-of-stroke switch which is closed when the relative angular displacement between the head 14 and the arm 72 exceeds a normal threshold of the order of ±7.5° and which automatically controls withdrawal of the carriage 71 and retraction of the head.

Figure 9:
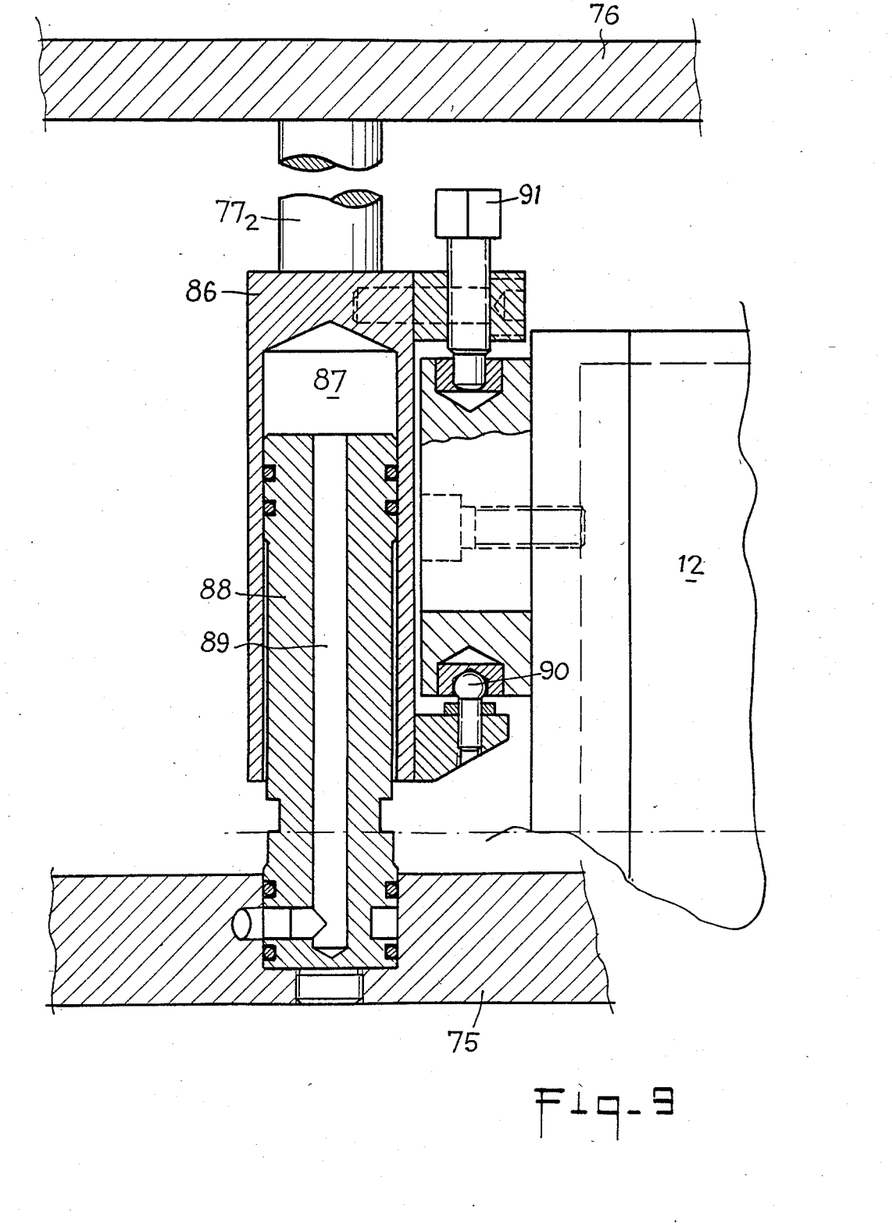
FIG. 9 is a partial vertical section through the sliding block connecting the detection head to the mobile frame.

FIG. 9 shows the connection between the detection head 12 and the frame 14. The Figure shows the lower plate 75 of the frame 14 which is connected to the upper plate 76 by two columns of hardened steel of which only one, $77_2$, is shown, and which serve to guide a sliding block 86. Inside the sliding block 86 is housed a cylinder 87 in which is located a piston 88 which abuts against plate 75.

The cylinder 87 and the piston 88 constitute a single-acting hydraulic jack which is supplied with oil via a duct 89 which passes through the piston.

Supply of oil of the jack is provided by an air-oil pressure exchanger which is installed in the arm 72.

When pressurized oil is sent into the cylinder, the head 12 bearing the sensors is raised. During the detection of the cracks, the jack lifting the head is not supplied and the head rests on the top of the slab under the effect of its weight. The head 12 is connected to the sliding block 86 by two ball joints 90 on which the head abuts and it is blocked by a screw 91.

Figure 10:
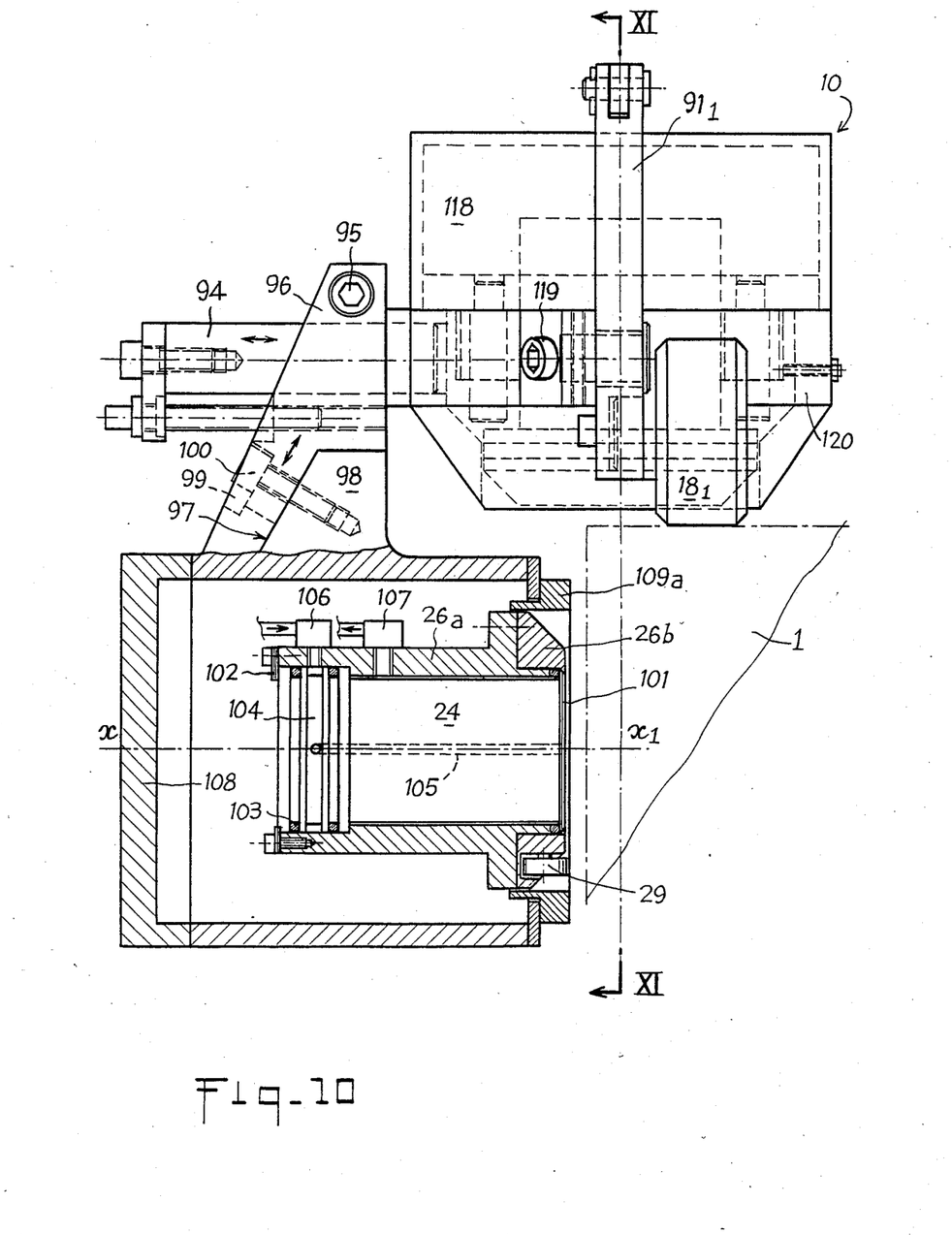
FIG. 10 is a side view, in elevation and in partial section, of the detection head.
Figure 11:
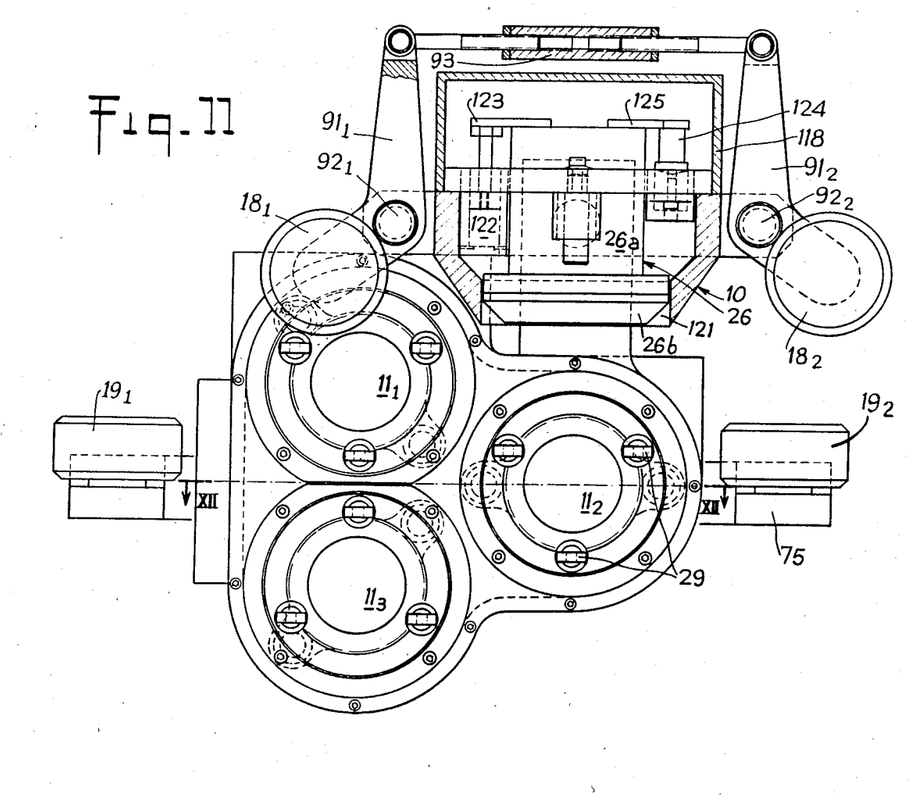
FIG. 11 is a section along XI—XI of FIG. 10.
Figure 12:
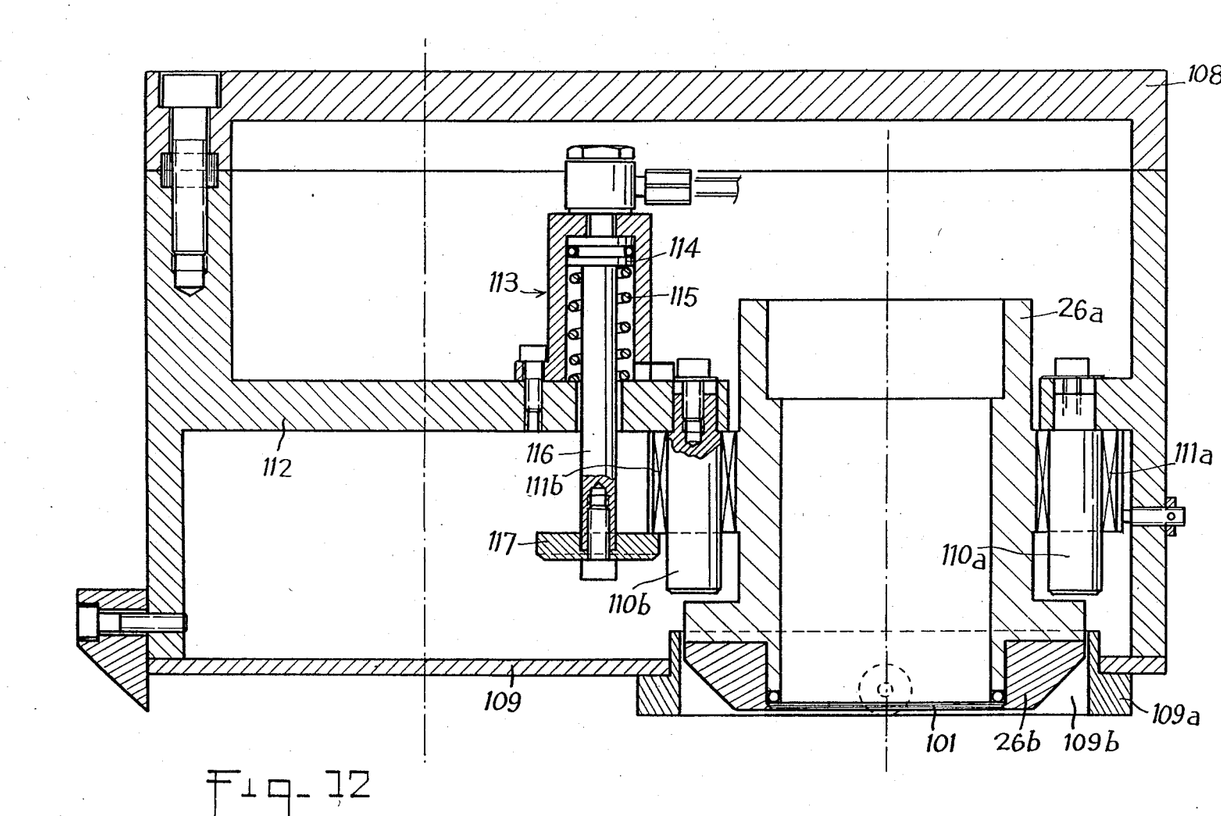
FIG. 12 is a section along XII—XII of FIG. 11.

FIGS. 10, 11 and 12 show views of the head 12 bearing the sensors.

FIG. 11 is a section of FIG. 10 along line XI—XI.

FIG. 12 is a horizontal section of FIG. 11 along line XII—XII.

FIG. 10 shows part of the side of a slab 1 and the top edge thereof.

FIG. 11 shows the two ends of the lower plate 75 in horse shoe form which each bear a vertical-axis roller $19_1$, $19_2$ located above the plate. As in the embodiment according to FIGS. 1 to 6, the head 12 bears three horizontal-axis crack sensors $11_1$, $11_2$ and $11_3$, disposed in a triangle and which are seen in front view in FIG. 10, and one vertical-axis sensor 10.

The head assembly is mounted on the sliding block 86 as shown in FIG. 9 and may therefore slide vertically. The head comprises two rollers $18_1$, $18_2$ whose axis is horizontal and transverse to the slab.

When the jack 88 is not supplied, these rollers roll on the top of the slab.

The rollers $18_1$ and $18_2$ are each borne by a bent lever $91_1$, $91_2$ articulated at $92_1$, $92_2$ on the head.

The ends of the two levers are connected together by a tension device 93 which enables the levers to be pivoted and the height of the rollers with respect to the head to be adjusted. The vertical sensor 10 is mounted on a transverse pin 94 which is blocked by a screw 95, in a split support 96, which enables the transverse position of the vertical sensor to be adjusted. The support 96 comprises an inclined ramp 97 which abuts on an inclined bearing surface, fast with a piece 98 itself fast with the casing which contains the three horizontal sensors. The support 96 comprises oval holes 99 and screws 100 which make it possible to displace the support 96 in height in order to adjust the height of the assembly of horizontal sensors with respect to the vertical sensor.

FIG. 11 shows a front view of the horizontal sensors and it is seen that the cap 26b of each sensor is equipped with casters 29 as in the embodiment shown in FIG. 4.

FIG. 10 shows an axial section through a horizontal sensor, which comprises a cylindrical casing 26a made of aluminium alloy and a cap 26b.

The front end of the cylindrical casing is obturated by a thin ceramic disc 101 which replaces the container 25 of the preceding embodiment. Inside the casing is located the coil 24 which detects the eddy currents. Said coil is maintained in the casing by a plate 102. The coil 24 is coated with an insulating resin. The outer wall and the bottom of the coil are separated by a clearance from the walls of the casing 26a and the disc 101.

The rear end of the coil comprises two O-rings 103 which are located on either side of a groove 104 which communicates with a cooling water inlet and with channels 105 which conduct the water into the space between the front face of the coil and the disc 101. References 106 and 107 represent the inlet of cold water and the return of water.

The three horizontal sensors $11_1$, $11_2$ and $11_3$ are disposed inside a chamber 108 into which slightly compressed air is sent. The front face of this chamber is closed by a plate 109 bearing three rings 109a which define three bores 109b disposed in a triangle and the cap 26b of each of the sensors slides with clearance in one of the bores, so that there is a leakage of compressed air through this clearance. Each sensor casing is mobile and acts as piston which is displaced under the effect of the thrust produced by the slight difference in pressure due to the leakage and this thrust maintains the rollers 29 applied against the slide of the slab and in this work position, the front end of the coil 24 lies a few millimeters from the side of the slab and separated therefrom by the ceramic disc 101 and by a film of water.

FIG. 12 shows that each horizontal sensor casing is guided in its displacement by two guide rods 110a, 110b and by ball bushes 111a, 111b with the result that there is very little friction. The rods 110a are borne by a partition 112 which forms part of the chamber 108.

FIG. 12 shows a pneumatic single-acting jack 113 which serves to repel the three horizontal sensors simultaneously.

The piston 114 of the jack is repelled rearwardly by a spring 115 antagonistic to the thrust of the compressed air. The rod 116 of the jack bears at its end a stop plate 117 which abuts against the ball bush 111b of the sensor.

To render the drawing clearer, FIG. 12 shows only one of the three horizontal sensors.

It is specified that jack 113 is placed at the centre of the three sensors and that the stop plate 117 abuts on the ball bushes guiding the three sensors.

FIG. 12 shows the sensor $11_2$ in retracted position which corresponds to the one where the jack 113 is not supplied with compressed air. The action of the return spring 115 maintains the three ball bushes in abutment against the partition 112 and the heads 26b are returned inside the chamber 108.

The compressed air which supplies jack 113 is the same as that which is sent inside chamber 108.

In this way, in the event of a failure in the compressed air supply, the three sensors are retracted automatically and simultaneously.

FIG. 11 shows an axial section through the vertical sensor 10, which is placed inside a vertical cylindrical casing 118 inside which compressed air is sent.

The casing 118 is fixed by screws 119 on a collar 120 which extends the pin 94 with the result that the height of the sensor may be adjusted with respect to the head.

The vertical sensor comprises, like each horizontal sensor, a mobile casing composed of a cylindrical body 26a and a cap 26b, and of a ceramic disc 101, inside which is placed a coil cooled by a circulation of water.

The bottom of the casing 118 comprises a circular orifice 121 of which the diameter is slightly larger than that of the cap 26b, so that there is a leakage between the periphery of the cap and the fixed casing 118. The casing 26 acts as piston and it is guided by ball bushes along two vertical columns not shown in the plane of section.

The vertical sensor comprises a return and lifting jack 122 which is a single-acting jack supplied with compressed air at the same time as the interior of the casing 118. The upper end of the rod of the jack 122 abuts against a stop plate 123, which is fixed to the mobile casing 26. The jack 122 comprises a return spring, antagonistic to the action of the compressed air. In the absence of compressed air, the spring pushes the plate 123 upwardly and maintains the vertical sensor in the raised position shown in FIG. 10. When the jack 118 is supplied with air, the spring is compressed and the mobile casing 26 is released and the rollers of the cap are maintained applied against the top of the slab by the thrust of the air and by its weight.

In the embodiment shown in FIG. 6, the weight of the mobile part of the vertical sensor is compensated by a counterweight. In the embodiment according to FIGS. 10, 11 and 12, the vertical sensor comprises a vertical pneumatic pressure loss jack 124 which is interposed between the fixed casing 118 and a stop plate 125 which is fixed to the mobile casing 26. The section of the piston and the supply pressure of this jack are calculated for the vertical thrust to balance the weight of the sensor, so that the latter is applied against the top of the slab by a weak vertical thrust which is due solely to the slight excess pressure of leakage inside the casing 118, so that the vertical sensor can follow the upper surface of the slab very faithfully.

What is claimed is:

1. A device for detecting cracks in steel slabs leaving a continuous casting installation by means of sensors employing eddy currents, which comprise an induction coil which is supplied with A.C. voltage and means for detecting variations in said voltage which indicate the presence of a crack, wherein said device comprises two crack detection units which are disposed on either side of the passage of the slabs, each unit comprising one vertical sensor which is maintained above the upper face of the slab, in the vicinity of an edge thereof, and a plurality of horizontal sensors which are located at different levels and which are maintained in the vicinity of a lateral face of the slab, two descaling and cooling units which are located on either side of the passage of the slabs, upstream of said detection units, and each descaling and cooling unit is mounted on a mobile frame which is displaced transversely with respect to the slab by a jack, and which bears one or more vertical axis rollers which are maintained applied against the side of the slab, descaling nozzles which project against the lateral face and against a band on the edge of the upper face of the slab jets of water at very high pressure, of the order of 150 bars, and cooling nozzles which spray the lateral face and the edge of the upper face of the slab.

2. The device of claim 1 wherein the descaling unit and the detection unit located on the same side of the slab are mounted on the same carriage which is displaced along an axis perpendicular to the longitudinal axis of the slab.

3. The device of claim 2 wherein each crack detection unit comprises a mobile frame which is equipped with vertical-axis casters and which is borne by an arm connected to said carriage by a vertical-axis articulation, which articulation comprises an oscillating jack which drives said arm in a rotation of the order of 90° to dispose it parallel to the side of the slab in work position and parallel to the axis of said carriage in rest position.

4. A device for detecting cracks in steel slabs leaving a continuous casting installation, which slabs have variable sizes and vertical side faces, by means of eddy-current sensors wherein said device comprises two crack detection units disposed on either side of the passage of the slabs and each crack detection unit comprises a mobile frame bearing one vertical sensor which is applied against the upper face of the slab, in the vicinity of an edge thereof, and a plurality of horizontal sensors which are applied against a side face of the slab, said mobile frame being equipped with horizontal-axis and vertical-axis casters, and said device further comprises means for displacing said mobile frame laterally and vertically with respect to the slab, and to maintain both said horizontal-axis casters applied against the upper face of the slab and said vertical-axis casters applied against a side face of the slab.

5. A device for detecting cracks in steel slabs leaving a continuous casting installation by means of eddy-current sensors, wherein said device comprises an axially mobile cylindrical casting having a ceramic bottom, a hollow cylindrical body and a cap which is fixed to the front end of said body and which is equipped with rollers whose rotation axes are perpendicular to the longitudinal axis of the slab and which are mounted on supports which slide parallel to the axis of said cylindrical body and said cap comprises locking screws for blocking said supports and adjusting the projection of said rollers with respect to the outer face of said cap, each sensor comprising an induction coil disposed coaxially inside the axially mobile cylindrical casing.

6. A device for detecting cracks in steel slabs leaving a continuous casting installation by means of eddy-current sensors, wherein said device comprises an axially mobile cylindrical casing guided axially by one or more ball bushes and pushed forwardly by a piston which moves with clearance in an axial bore and which is subjected to a forward thrust which is due to the loss of pressure produced by a leakage of air around said piston and equipped rollers applied against the surface of the slab with a weak, constant thrust, each sensor comprising an induction coil disposed coaxially inside the axially mobile cylindrical casing.

7. The device of claim 6, wherein each sensor is associated with an auxiliary single-acting pneumatic jack which is supplied with air in parallel with said leakage of air and which comprises a spring antagonistic to the air pressure and the rod of said jack bears a stop which blocks said sensor in retracted position in the event of accidental cut-off of air or at the end of cycle.

8. The device of claim 6, wherein the vertical sensor of each detection unit comprises a counterweight which balances the weight of the mobile part of said sensor.

9. The device of claim 6, wherein the vertical sensor of each detection unit comprises a balancing jack which balances the weight of the mobile part of said sensor.

10. A device for detecting cracks in steel slabs leaving a continuous casting installation by means of eddy-current sensors wherein said device comprises two crack detection units disposed on either side of the passage of the slabs and each crack detection unit comprises a mobile frame which is equipped with vertical-axis casters and means for displacing said frame laterally with respect to the slab and to maintain said casters applied against a side of the slab, wherein said mobile frame is supported by two parallel arms forming a parallelogram articulated, respectively, on said mobile frame by vertical-axis articulations and on a fixed frame by other vertical axis articulations and one of said arms is actuated by means of a double-acting jack to displace said mobile frame laterally with respect to the slab and wherein one of said arms comprises a telescopic device which allows a slight variation in length of said arm and a limited rotation of said frame, and it further comprises a displacement sensor which detects a variation in length of said arm exceeding a limiting value and which automatically controls said jack.

11. A device for detecting cracks in steel slabs leaving a continuous casting installation by means of eddy-current sensors wherein said device comprises two crack detection units and two descaling units disposed on either side of the passage of the slabs and the descaling unit and the crack detection unit located on the same side of the slabs are mounted on the same carriage which is displaced along an axis of the slab wherein each crack detection unit comprises a mobile frame which is borne by an arm connected to said carriage by a vertical-axis articulation which articulation comprises an oscillating jack which drives said arm in rotation to dispose it parallel to the side of the slab in work position wherein said mobile frame comprises a lower plate, an upper plate and three columns which connect said plates and said mobile frame is connected to said arm by one of the three columns which comprises a flat portion on which abuts a roller which is disposed at the end of a finger which slides in a radial bore in said arm and which is pushed by an elastic member and which further comprises a threaded stopper making it possible to adjust the pre-stress of the elastic member, which stopper comprises an axial threaded bore in which penetrates a rod fast with said finger and in which a screw, serving as an adjustable stop for said rod, is disposed.

12. A device for detecting cracks in steel slabs leaving a continuous casting installation by means of eddy-current sensors wherein said device comprises two crack detection units disposed on either side of the passage of the slabs and each crack detection unit comprises a mobile frame which is equipped with vertical-axis casters and means for displacing said frame laterally with respect to the slab and to maintain said casters applied against a side of the slab wherein said mobile frame comprises guide columns and each detection unit comprises a detection head which slides vertically along said columns and which bears said sensors and is equipped with rollers of transverse horizontal axis which are maintained applied against the upper face of the slab by the weight of the sliding head, and each detection unit further comprises a vertical single-action jack which lifts said sliding head at the end of a cycle wherein said sliding head further comprises a chamber having a vertical front face closed by a plate which bears three rings which are disposed in a triangle and which each defines a bore and said sliding head comprises three horizontal sensors each placed inside a horizontal mobile cylindrical casing which casing comprises a hollow cylindrical body and a cap fixed to the front end of said body and each cap is engaged with clearance in one of said three bores and said chamber is supplied with compressed air at low pressure which escapes through said clearances.

13. The device of claim 12, wherein said detection head comprises a single-acting pneumatic jack of horizontal axis which is disposed in the axis of the three horizontal sensors, which jack comprises an antagonistic spring and the rod of said jack bears a stop plate which abuts against the mobile casings of the three sensors, so that said jack simultaneously releases the three horizontal sensors and it retracts them simultaneously in the event of cut-off of compressed air.

* * * * *